United States Patent [19]

Foster

[11] Patent Number: 5,854,176
[45] Date of Patent: Dec. 29, 1998

[54] CONDITIONING OF HERBICIDAL CHLOROACETAMIDES

[75] Inventor: John M. Foster, Fort Collins, Colo.

[73] Assignee: Sandoz Ltd., Basel, Switzerland

[21] Appl. No.: 813,095

[22] Filed: Mar. 7, 1997

Related U.S. Application Data

[63] Continuation of Ser. No. 491,180, Jun. 16, 1995, abandoned.

[51] Int. Cl.$^6$ .......................... A01N 25/32; A01N 43/00; A01N 43/10; A01N 43/72
[52] U.S. Cl. .......................... 504/105; 504/129; 504/131; 504/222; 504/289
[58] Field of Search .................................... 504/105, 129, 504/131, 222, 289

[56] References Cited

U.S. PATENT DOCUMENTS

| | | | |
|---|---|---|---|
| 3,708,277 | 1/1973 | Zeidler et al. | 71/91 |
| 4,666,502 | 5/1987 | Seckinger et al. | 71/90 |
| 5,457,085 | 10/1995 | Seckinger et al. | 504/289 |

*Primary Examiner*—Allen J. Robinson
*Attorney, Agent, or Firm*—Bell Seltzer Intellectual Property Law Group of Alston & Bird, L.L.P.

[57] ABSTRACT

There is provided a method for protecting crop plants from phytotoxic injury caused by a chloroacetamide herbicide by co-applying a non-phytotoxic, conditioning effective amount of a benzothiadiazinone derivative. The method is particularly effective in protecting dry edible beans from phytotoxicity when dimethenamid is applied postemergence.

16 Claims, No Drawings

CONDITIONING OF HERBICIDAL CHLOROACETAMIDES

This application is a continuation of application Ser. No. 08/491,180, filed Jun. 16, 1995, now abandoned.

BACKGROUND OF THE INVENTION

While herbicides have gained a high degree of commercial success because it has been shown that such compounds can increase crop yields and reduce harvesting costs, some of these herbicides have been shown to injure crop plants at rates necessary to control weed growth. To be effective, a herbicide must cause minimal damage, and preferably no damage to the beneficial crop while maximizing damage to weed species which infest the locus of a crop. The injury caused by various known herbicides varies depending on a number of factors some of which include the type of herbicidal formulation applied to the crop plants, the type of crop, the type of soil a crop is growing in and environmental factors such as temperature or wetness. While a herbicide may not injure a crop plant under one set of conditions, it is possible that the same herbicide could cause injury under a different set of conditions.

To protect a crop species from herbicidal injury along with concomitant herbicidal effectiveness on weed species, use of chemical compounds called safeners or antidotes have been employed. The use of safeners with herbicidally active compounds is a widely accepted agricultural practice. Safeners are used on crops including agronomic and vegetable species. The terms safener, safening agent, antidote, antagonistic agent and crop protectant are often used terms in the art and denote a compound capable of reducing the phytotoxicity of a herbicide to a crop plant or crop seed but which is not phytotoxic itself to the crop plant or crop seed and which does not affect the herbicides' activity against targeted weeds.

Crop species susceptible to herbicidal injury may also benefit from the use of compounds called conditioners. Unlike safeners, these compounds are herbicidal to some undesirable plant species when applied at conditioning rates; but like safeners, conditioners lower the phytotoxic effect of herbicidal compounds on a crop plant or seed without being phytotoxic itself to the crop plant.

The chloroacetamide herbicide known as dimethenamid has been found to be a very effective herbicide with broad general activity against a wide variety of undesirable weed species. Chloroacetamides and particularly thiophene based chloroacetamides (hereinafter referred to as "thiopheneamides") including dimethenamid are disclosed in U.S. Pat. No. 4,666,502. Additionally, the (S) optical isomer of dimethenamid is disclosed in U.S. Pat. No. 5,457,085 (application Ser. No. 310,198, filed Sep. 21, 1994). Both of these U.S. Patents are incorporated herein in their entirety by reference. Dimethenamid is commercially available, for example, under the trade name FRONTIER herbicide (Sandoz Crop Protection, Inc., Des Plaines Ill.)

Although selective in many major crops, in certain specific crops dimethenamid has been found to adversely effect or interfere with the culture of the desirable crop species. Therefore the effective use of the herbicide for controlling weeds in the presence of such crops or under specific conditions is further enhanced by the addition of conditioners and/or safeners.

It is therefore an object of the present invention to provide a method of reducing phytotoxicity to a crop plant due to the injury caused by a thiopheneamide herbicide without decreasing the herbicidal efficacy of said thiopheneamide which comprises applying to the crop plant or a locus where control of undesirable weeds is desired an effective conditioning amount of a benzothiadiazinone derivative.

It is also an object of the present invention to provide a herbicidal composition comprising a herbicidally effective amount of a thiopheneamide herbicide in combination with a non-phytotoxic, conditioning-effective amount of a benzothiadiazinone compound.

These and other objects of the present invention will become more apparent from the detailed description set forth below.

SUMMARY OF THE INVENTION

The present invention relates to a method for reducing the phytotoxicity of a herbicidally effective amount of a thiopheneamide compound on a crop plant comprising co-applying to the crop plant or locus where herbicidal control is desired an non-phytotoxic, conditioning-effective amount of a conditioner compound having the structural formula (B)

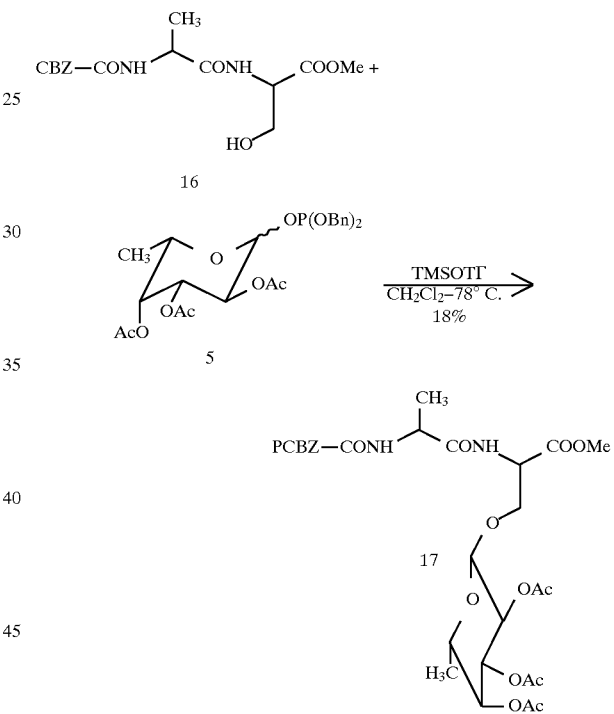

wherein R is $C_{1-6}$ alkyl.

Preferably, the method comprises co-applying to the crop plant or a locus where control is desired a herbicidally effective amount of a thiopheneamide compound of formula (A)

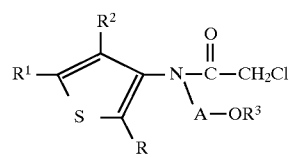

wherein R and $R^2$ are independently H, Cl, Br, F, $C_{1-4}$ alkyl and $C_{1-4}$ alkoxy; $R^1$ is H, Cl, Br, F, or $C_{1-4}$ alkyl; $R^3$ is $C_{1-8}$ alkyl; and A is $CH_2$, $CH_2$—$CH_2$ or a monomethylated derivative thereof and a non-phytotoxic, conditioning-effective amount of a compound according to formula (B).

DETAILED DESCRIPTION OF THE INVENTION

The present invention relates to a method of reducing the phytotoxicity of a herbicidally effective thiopheneamide compound comprising applying a compound of formula (B), defined herein as a conditioner, to the seed of the crop to be conditioned, to the foliage of the crop or to the soil surrounding the crop or crop seed. The herbicidal compounds and the conditioner compounds of this invention are known in the art.

Herbicides which are suitable for use in the present invention include thiopheneamide herbicides as generally disclosed in U.S. Pat. No. 4,666,502 along with methods of their production. An especially preferred compound is (RS)-2-chloro-N-(2,4-dimethyl-3-thienyl)-N-(2-methoxy-1-methylethyl) acetamide, a commercially available herbicide known by the common name "dimethenamid". Also preferred are derivatives of dimethenamid including salts and esters as well as isomers thereof. Although dimethenamid and some of its derivatives have been used with success in certain crops, dimethenamid has been found to be phytotoxic in certain crops and under certain environmental conditions when applied at rates necessary for effective control of undesired vegetation.

Surprisingly it has been found that thiopheneamide herbicides can be conditioned by applying to the crop plant or locus where control of undesirable weed species is desired a benzothiadiazinone dioxide of formula B. The preferred conditioner compound of the present invention is 3-isopropyl-1H-2,1,3-benzothiadiazin-4(3H)-one 2,2-dioxide, known by the common name "bentazone" or "bentazon". Bentazon(e) is a well known compound and disclosed in U.S. Pat. No. 3,708,277 along with methods for its production. Bentazon(e) is also used as a herbicide; it is generally used as a selective postemergence herbicide for the control of specific broadleaf weeds, such as common cocklebur, velvetleaf, ragweeds and the like. Bentazon(e) does not control grasses and therefore is used in conjunction with other grass- and broadleaf weed herbicides.

The terms "herbicide" or "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn and dwarfing. The term "herbicidally-effective" is defined as the amount of herbicide which controls or causes a modifying effect when applied to the undesired plants themselves or to the area or locus where control or modification is desired. The term locus may include soil, seed, seedlings, the crop plant, crop seed, weed plant and vegetation. The term "plant or plants" is meant to include germinate seed, emerging seedlings, rhizomes and established vegetation.

The term safener, antidote and other like terms denote a compound which is capable of reducing the phytotoxicity of an herbicide to a crop plant, is non-phytotoxic to the crop plant, and is not herbicidal to plants when applied at a safening effective rate.

The term "conditioner" as used herein is defined as a compound which is capable of reducing the phytotoxicity of a thiopheneamide herbicide to a crop plant, is non-phytotoxic to the crop plant and is herbicidal to some weed species when applied at effective conditioning amounts. Additionally, the conditioner as defined herein does not adversely affect the herbicidal activity of a thiopheneamide when the conditioner is used in combination with the thiopheneamide compound. While the conditioning compounds of this invention are herbicidal themselves, it will be appreciated by one skilled in the art, that a conditioning compound may not be herbicidal for all weeds.

The term "non-phytotoxic" is defined as an amount of safener or conditioner which causes at most minor injury or no injury to the desired crop species.

The term "conditioning-effective amount" is defined as the amount of conditioner required to decrease the extent of injury caused by a thiopheneamide herbicide to the desired crop species. Phytotoxicity or injury to a desired crop species is manifested in numerous ways well known to those skilled in the art and includes without limitation, leaf burning, leaf distortion, stunting, leaf spotting and all deviations from natural development and acceptable development.

A preferred embodiment of the invention comprises a method of reducing the phytotoxicity of a thiopheneamide herbicide to a crop plant comprising applying to the crop plant or locus where herbicidal control is desired a herbicidally effective amount of a thiopheneamide herbicide and a non-phytotoxic, conditioning-effective amount of 3-isopropyl-1H-2,1,3-benzothiadiazin-4(3H)-one 2,2-dioxide.

Another embodiment of the invention includes a herbicidal composition comprising a herbicidally effective amount of a thiopheneamide herbicide in combination with a non-phytotoxic, conditioning-effective amount of a benzothiadiazinone compound wherein the injury caused to a crop plant from the thiopheneamide herbicide is reduced by the conditioning compound.

The conditioning of crops from the postemergence application of thiopheneamide herbicides may be effected by allowing the crop plant to grow until for example, the unifoliate or trifoliate leaf stage then spraying with an aqueous solution of the invention. Additionally the invention may be practiced by applying a composition of the invention to the soil preemergence. However, the thiopheneamide compound and conditioner are applied in co-application. Co-application is understood to mean concurrent, or immediate sequential application (within 24 hours), application as a tank mix or application of fixed combination premixes.

The present invention may be used as a means of controlling a large range of broadleaf and grassy weeds in a crop locus wherein the crops include for example, cereals, such as corn; leguminous crops, such as soybean, peanuts, Phaseolus beans, and dry edible beans; cotton; sugarbeet; and sunflower. In a preferred embodiment the invention can be used to selectively control undesirable plants when the crop plant is a leguminous plant and wherein the chloroacetamide herbicide, and in particular a thiopheneamide herbicide, causes phytotoxicity to the leguminous crop plant. Therefore, the invention further includes a method of protecting a leguminous crop plant from injury due to a chloroacetamide herbicide comprising co-applying to the plant or a locus where herbicidal control is desired a herbicidally effective amount of a chloroacetamide herbicide and a non-phytotoxic conditioning effective amount of a compound corresponding to the formula

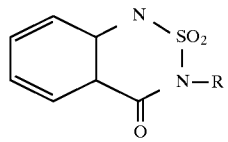

wherein R is $C_{1-6}$alkyl and said conditioner being conditioning active with said chloroacetamide herbicide on said leguminous crop plant.

The amount of a given conditioner to be utilized in combination with the herbicide of this invention and the manner of its utilization and resulting efficacy can vary according to various parameters such as the particular conditioner to be applied, the crop which is to be protected, the amount or rate of herbicide to be applied and the soil and climatic conditions of the agricultural environment in which the mixture is to be applied. The selection of a specific conditioner for use in the herbicidal composition, the manner in which it is to be applied (for example, tank mix, in-furrow application or seed treatment) and the determination of activity which is conditioning can be readily performed utilizing test procedures in accordance with common practice in the art.

Although the weight ratio of thiopheneamide herbicide and conditioner will vary depending upon the crop to be protected, weed to be inhibited and the specific herbicidal compound and conditioner used, the ratio will be in the range of from about 0.1:1.0 to about 30:1 (exclusive of auxiliary ingredients). A preferred weight ratio is from about 15:1 to about 1:15. An even more preferred weight ratio is 5:1 to about 1:5. In general, the effective thiopheneamide herbicidal amounts are in the range of about 0.01 to about 8.0 kg/ha. The preferred range is from about 0.1 to about 4.0 kg/ha and more preferred is the range from about 0.2 to about 3.0 kg/ha.

The effective conditioning amount of a conditioner will usually be determined on economic ratios for the most effective amount usable. It is understood that a non-phytotoxic amount of a conditioning compound with respect to a particular crop plant will be employed. However, the amount used may also have an herbicidal effect on undesirable plant species and therefore have an additive or even synergistic effect when used in combination with the thiopheneamide herbicides disclosed herein. The amount of conditioner will generally be in the range of about 0.01 to about 10.0 kg/ha and a preferred range is from about 0.1 to about 4.0 kg/ha.

The compounds of the invention can be formulated in the same manner in which herbicides are generally formulated. The object of the formulation is to apply the compounds to the locus where control is desired by conventional methods.

Useful formulations of the invention include dusts, granules, microcapsules, pellets, solutions, suspensions, emulsions, emulsifiable concentrates and the like. They are obtained by conventional manner, e.g. by mixing the compounds with diluent(s). Many of these can be applied directly to the locus. Application of the thiopheneamide herbicide and conditioner for co-application will vary depending upon climatic conditions, season weeds to be controlled and the like. In general, the formulations include from about 0.01% to 99% by weight of the active herbicide and conditioner ingredients and optionally at least about 0.1% to about 20% surfactant or 1% to about 99.9% solid or liquid inert diluent(s). Surfactant as used herein means a herbicidally acceptable material which imparts emulsifiability, spreading, wetting, dispersiblity or other surface-modifying properties. Diluent as used herein means a liquid or solid herbicidally acceptable material used to dilute a concentrated material to a useable or desirable strength.

BIOLOGICAL EVALUATION

The following examples are provided for illustrative purposes only and are not intended to limit the invention in any way.

EXAMPLE 1

Postemergence Weed Control in Dry Edible Beans:

Dry edible Great Northern beans seeds (Beryl) are planted in field plots 15 feet wide by 40 feet long in sandy loam soil with 1% organic matter and pH 7.8 in Nebraska. The experimental design is a randomized complete block with 4 replicates. Post emergence treatments of herbicide and conditioner are applied at the unifoliate leaf stage, approximately 14 days after planting. Compounds are applied with a tractor mount sprayer calibrated to deliver 21 gallons per acre. Herbicide and conditioner treatment included X-77 at a rate of 25% per volume of carrier and nitrogen 28% (N) is added at a rate of 2.5% per volume of carrier. X-77 is a non-ionic wetting agent containing alkylaryl polyoxyethylene, glycols, free fatty acids and isopropanol (Valent, Richmond, Calif.). Dry edible bean visual injury in the form of leaf chlorosis, browning and plant stunting is evaluated 4, 11, 18 and 24 days after treatment. Visual injury is reported on a scale of 0 to 100 with 0 equal to no injury and 100 equal to complete kill in Table 1. Bean yield is determined 2 months after planting. The results are summarized in Tables 1 and 2 wherein F is FRONTIER herbicide, (RS)-2-chloro-N-(2,4-dimethyl-3-thienyl)-N-(2-methoxy-1-methylethyl) acetamide, (common name "dimethenamid" [Sandoz Crop Protection, Des Plaines, Ill.]);

B is the conditioner, BASAGRAN herbicide, 3-isopropyl-1H-2,1,3-benzothiadiazin-4(3H)-one 2,2-dioxide; (common name "bentazon(e)" [BASF Corp, Research Triangle Park, N.C.]);

AMARE is redroot pigweed; CHEAL is common lambquarters; SOLSA is hairy nightshade; POROL is common purslane and ECHCG is barnyardgrass.

TABLE 1

| | Conditioning of Dimethenamid by Bentazon(e) | | | | | |
|---|---|---|---|---|---|---|
| Herbicide + | Rate | % Injury (days after treatment) | | | | Bean Yield |
| Conditioner | (lb a.i./a) | 4 | 11 | 18 | 24 | (bu/a) |
| Untreated | | 0.0 | 0.0 | 0.0 | 0.0 | 35 |
| B | 0.5 | 0.0 | 0.0 | 5.3 | 1.3 | 54 |
| F + B | 1.0 + 0.5 | 5.0 | 3.8 | 3.8 | 0.0 | 61 |
| F | 1.0 | 30.0 | 30.0 | 16.3 | 9.5 | 39 |

TABLE 2

Mean Percent Weed Control 24 Days After Treatment

| Herbicide + Conditioner | Rate (lb a.i./A) | AMARE | CHEAL | SOLSA | POROL | ECHCG |
|---|---|---|---|---|---|---|
| Untreated | — | 20 | 21 | 21 | 33 | 20 |
| B | 0.5 | 40 | 74 | 81 | 81 | 28 |
| F + B | 1.0 + 0.5 | 98 | 99 | 99 | 99 | 97 |
| F | 1.0 | 52 | 52 | 59 | 99 | 97 |

It is claimed:

1. A method for reducing the phytotoxicity of a herbicidally effective amount of a thiopheneamide compound on a crop plant comprising co-applying to the crop plant or locus where herbicidal control is desired a non-phytotoxic, conditioning-effective amount of a conditioner compound having the formula (B)

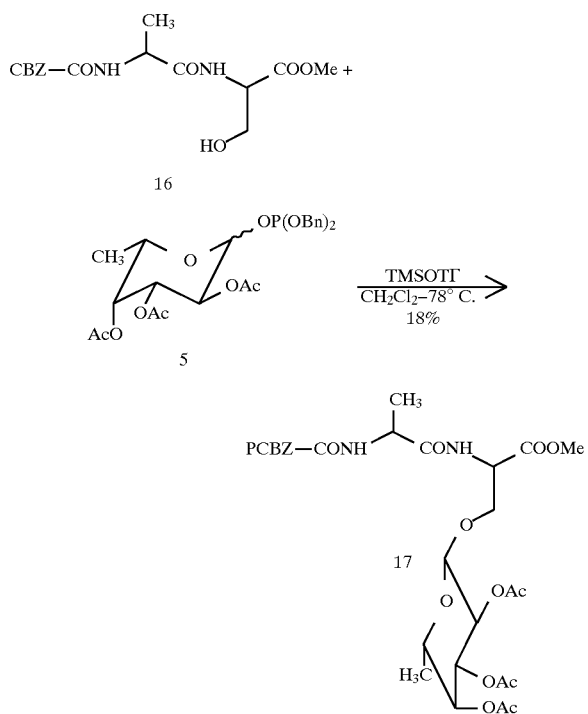

wherein R is $C_{1-6}$alkyl and a herbicidally active thiopheneamide of formula A

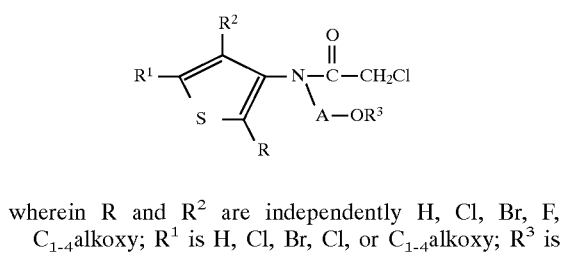

wherein R and $R^2$ are independently H, Cl, Br, F, $C_{1-4}$alkoxy; $R^1$ is H, Cl, Br, Cl, or $C_{1-4}$alkoxy; $R^3$ is $C_{1-8}$alkyl; and A is $CH_2$, $CH_2$—$CH_2$ or a monomethylated derivative thereof, wherein the weight ratio of the thiopheneamide compound to the conditioner compound is in the range of 0.1:1.0 to 30:1 and the thiopheneamide compound is applied at a range of 0.01 to 8.0 kg/ha and the conditioner is applied at a range of 0.01 to 10.0 kg/ha.

2. The method according to claim 1 wherein the thiopheneamide herbicide is (RS)-2-chloro-N-(2,4-dimethyl-3-thienyl)-N-(2-methoxy-1-methylethyl) acetamide.

3. The method according to claim 1 wherein the thiopheneamide herbicide is (S)-2-chloro-N-(2,4-dimethyl-3-thienyl)-N-(2-methoxy-1 -methylethyl) acetamide.

4. The method according to claim 1 wherein the thiopheneamide herbicide is (RS)-2-chloro-N-(2,4-dimethyl-3-thienyl)-N-(2-methoxy-1-methylethyl) acetamide and the conditioner is 3-isopropyl-1H-2,1,3-benzothiadiazin-4(3H)-one 2,2-dioxide.

5. The method according to claim 1 wherein the weight ratio of thiopheneamide herbicide to conditioner ranges from about 5:1 to about 1:5.

6. The method of claim 1 wherein the thiopheneamide and the conditioner are each independently applied at a rate of 0.1 to 4.0 kg/ha.

7. A method for protecting crop plants from injury caused by a herbicidally effective amount of a thiopheneamide of formula A

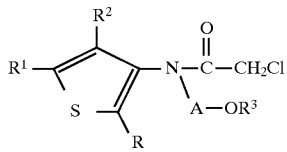

wherein R and $R^2$ are independently H, Cl, Br, F, $C_{1-4}$alkyl and $C_{1-4}$alkoxy; $R^1$ is H, Cl, Br, F, or $C_{1-4}$alkyl; $R^3$ is $C_{1-8}$alkyl; and A is $CH_2$, $CH_2$—$CH_2$ or monomethylated derivative thereof comprising co-applying a non-phytotoxic, effective conditioning amount of 3-isopropyl-1H-2,1,3-benzothiadiazin-4(3H)-one 2,2-dioxide and the thiopheneamide compound, wherein the thiopheneamide and conditioner are applied at a weight ratio of 15:1 to about 1:15.

8. The method according to claim 7 wherein the thiopheneamide is the herbicide known as dimethenamid.

9. The method according to claim 7 wherein the thiopheneamide is the (S) isomer of dimethenamid.

10. The method according to claim 7 wherein the herbicide and conditioner are applied postemergence.

11. The method according to claim 7 wherein the herbicide and conditioner are applied preemergent.

12. The method according to claim 1 wherein the herbicide and conditioner are applied separately.

13. The method according to claim 1 wherein the herbicide and conditioner are co-applied in a tankmix.

14. The method according to claim 7 wherein the crop plant is a leguminous plant.

15. The method according to claim 14 wherein the leguminous plant is a bean plant.

16. The method according to claim 7 wherein the crop plant is maize.

* * * * *

UNITED STATES PATENT AND TRADEMARK OFFICE
CERTIFICATE OF CORRECTION

PATENT NO. : 5,854,176
DATED : December 29, 1998
INVENTOR(S) : Foster

It is certified that error appears in the above-identified patent and that said Letters Patent is hereby corrected as shown below:

Column 2, beginning with line 21 and continuing through line 49, the formula should appear as follows:

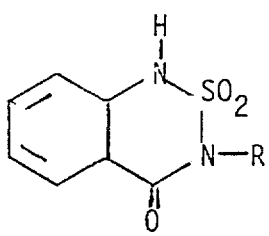

UNITED STATES PATENT AND TRADEMARK OFFICE
CERTIFICATE OF CORRECTION

PATENT NO. : 5,854,176

DATED : December 29, 1998

INVENTOR(S) : Foster

It is certified that error appears in the above-identified patent and that said Letters Patent is hereby corrected as shown below:

Column 7, Claim 1, beginning with line 21 and continuing through line 49, the formula should appear as follows:

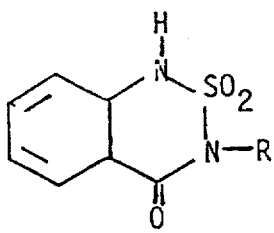

Signed and Sealed this

Eighteenth Day of May, 1999

Attest:

Q. TODD DICKINSON

Attesting Officer

Acting Commissioner of Patents and Trademarks